United States Patent [19]

Puskas et al.

[11] Patent Number: 4,467,110

[45] Date of Patent: Aug. 21, 1984

[54] PROCESS FOR PURIFICATION OF CRUDE TEREPHTHALIC ACID

[75] Inventors: Imre Puskas, Glen Ellyn; David E. James, Batavia, both of Ill.

[73] Assignee: Standard Oil Company (Indiana), Chicago, Ill.

[21] Appl. No.: 466,651

[22] Filed: Feb. 15, 1983

Related U.S. Application Data

[62] Division of Ser. No. 316,338, Oct. 29, 1981, Pat. No. 4,394,299.

[51] Int. Cl.³ .............................................. C07C 51/42
[52] U.S. Cl. .................................... 562/487; 502/185; 502/230; 562/485
[58] Field of Search ................ 562/485, 487; 502/185, 502/230

[56] References Cited

U.S. PATENT DOCUMENTS

| 3,265,729 | 8/1966 | Olsen et al. | 562/487 |
| 3,522,298 | 7/1970 | Bryant et al. | 562/487 |
| 3,542,863 | 11/1970 | Zimmerschied | 562/487 |
| 3,546,285 | 12/1970 | Witt | 562/487 |
| 3,584,039 | 6/1971 | Meyer | 562/487 X |
| 3,591,629 | 7/1971 | Stancell et al. | 562/487 |
| 3,607,921 | 9/1971 | Stancell et al. | 562/487 |
| 3,726,915 | 4/1973 | Pohlmann | 562/487 |
| 3,799,976 | 3/1974 | Nienburg et al. | 562/487 |
| 4,260,817 | 4/1981 | Thompson et al. | 562/487 |

Primary Examiner—Natalie Trousof
Assistant Examiner—Vera C. Clarke
Attorney, Agent, or Firm—William C. Clarke; William T. McClain; William H. Magidson

[57] ABSTRACT

A process for producing a purified terephthalic acid which comprises reacting in a liquid phase a mixture of hydrogen and crude terephthalic acid, a palladium/-rhodium catalyst on a porous carbonaceous support wherein the catalyst compound is prepared by adsorbing palladium on the support from a complex salt formed in the presence of an amine and acetic acid, followed by deposition of rhodium from a solution of sodium hexanitritorhodate.

12 Claims, No Drawings

PROCESS FOR PURIFICATION OF CRUDE TEREPHTHALIC ACID

This is a division of application Ser. No. 316,338 filed Oct. 29, 1981 now U.S. Pat. No. 4,394,299.

BACKGROUND OF THE INVENTION

Purification of crude terephthalic acid by hydrogenation over a suitable catalyst is well-known. Hydrogenation offers the easiest route for removal of 4-carboxybenzaldehyde (4-CBA) impurity from the crude terephthalic acid (TA). This invention is directed to an improved process for the hydrogenation of crude terephthalic acid in the presence of a catalyst prepared by utilizing palladium and rhodium metals deposited upon an active carbon support from water-soluble precursors to produce a catalyst of improved activity and/or selectivity in hydrogenating 4-carboxybenzaldehyde to very low levels. Under severe test conditions, 4-carboxybenzaldehyde content is decreased to less than 100 parts per million (ppm) and p-toluic acid content increase is minimized.

Catalysts comprising a Group VIII metal of the Periodic Table upon an inert carrier are known for use in various hydrogenation reactions. They are usually prepared by impregnating a support material with a solution of a compound of a Group VIII metal and reducing the impregnated compound to the metal. Catalyst improvements typically have been directed to obtaining increased hydrogenation activity rather than increased activity and/or selectivity in hydrogenating specific compounds.

It is an object of the instant invention to provide an improved method for preparing a catalyst compound of a Group VIII metal. A particular object is to provide a method for preparing such catalysts having increased catalytic activity and/or selectivity in the reduction of 4-carboxybenzaldehyde. Another object is to provide a catalyst composition which comprises involving the preparation of complex salts of Group VIII metals wherein a catalyst of improved selectivity is obtained for use in reduction of 4-carboxybenzaldehyde in purification of crude terephthalic acid containing up to 10,000 ppm of 4-carboxybenzaldehyde. Still further objects will be apparent from the following specification.

The field of this invention accordingly relates to Group VIII metal catalysts for hydrogenation and purification of terephthalic acid suitable for polyester polymers and copolymers useful in the manufacture of textile fibers. These polymers and copolymers have been made by condensing terephthalic acid with ethylene glycol and other dihydric alcohols.

Such Group VIII catalysts are limited in their ability to selectively hydrogenate impurities in the terephthalic acid, especially 4-carboxybenzaldehyde. Users of terephthalic acid, such as textile fiber manufacturers, often put a rigorous limitation on the allowable concentration of 4-carboxybenzaldehyde in terephthalic acid.

As with other supported catalysts, the activity and selectivity of a Group VIII metal catalyst upon a carrier depends on numerous factors such as the amount of Group VIII metal or metals present in the catalyst, the type of support, the method by which the Group VIII metal is deposited and the distribution of the metal on the support. Improvement of Group VIII metal catalysts has typically been of activity rather than of selectivity.

Group VIII metal catalysts, such as palladium catalysts, useful in hydrogenation processes often are prepared by causing a Group VIII metal salt, such as a palladium salt, to be absorbed from a solution onto a carrier. In one procedure as is taught in U.S. Pat. No. 2,857,337, a palladium salt is thereupon treated with a water-soluble metal hydroxide or basic carbonate which is thereafter reduced to metallic palladium by reducing agents such as formaldehyde, glucose, hydrazine, glycerine and the like. Catalysts prepared by the '337 process are particularly useful in improved catalytic activity in reduction of aromatic nitro compounds to the corresponding amines.

Other conventional methods of preparing palladium catalysts have been taught. U.S. Pat. No. 2,802,794 teaches impregnation of an activated alumina support material with a solution of a compound of the platinum metal group and reducing the impregnated compound to the metal. The preconditioned activated alumina is obtained by heating a hydrated alumina to a temperature of up to 800° C. whereby a microporous alumina is obtained. The resulting catalyst showed increased catalytic activity in hydrogenating butylanthraquinone to butylanthrahydroquinone.

U.S. Pat. No. 3,138,560 to Keith, et al., teaches that when sodium tetrachloropalladate or palladium chloride is added to many carbon supports, most of the palladium is immediately deposited as a shiny film of metallic palladium. Catalysts so prepared generally have low activities and it has been theorized that the palladium compound is directly reduced to palladium metal by the presence of functional groups, such as aldehydes or free electrons on the carbon surface. Palladium catalysts are accordingly taught as advantageously prepared by fixing the palladium as an insoluble compound prior to reduction to avoid the problems of migration and crystallite growth which can occur when a metal is reduced from solution. Keith '560 teaches inclusion of an oxidizing agent, such as hydrogen peroxide, to hydrolyze the palladium prior to reduction by the carbon, thus obtaining improved palladium dispersion and a highly active catalyst for the reaction of oxygen with hydrogen to give water. U.S. Pat. No. 3,288,725 to Aftandilian teaches that catalysts produced by deposition of a transition metal compound upon an inert particulate solid and subsequent reduction often have a disadvantage in that uniform deposition of the transition metal compound upon the surface of the inert particulate is accomplished with great difficulty. Hence, when the metal compound is reduced, the metal atoms deposited on the surface thereof are not exposed, are therefore not completely reduced and maximum potential catalytic activity is not achieved. Aftandilian '725 teaches that reaction of the metal compound with a particulate surface having a suitable hydroxyl group content, followed by reduction with a borohydride produces an improved catalyst for hydrogenation of unsaturates to saturates and nitro compounds to amines. U.S. Pat. No. 3,737,395 to Arnold, et al., teaches a process for preparing a catalyst which avoids formation of gels which cause lower activity. The catalysts, useful in hydrogenating unsaturated compounds such as maleic acid, are taught as having uniform and controlled deposition of palladium or platinum and a metallic promoter onto particulate carbon. An aqueous slurry is formed of the palladium or platinum compound and the water soluble metallic promoter. A precipitant is then added to precipitate the palladium or platinum and the metallic promoter, followed by co-reduction of both with a mild reducing agent such as formaldehyde, hydrazine, sodium formate, glucose or hydrogen. U.S. Pat. No. 3,271,327 to McEvoy, et al., teaches a process for depositing palladium upon the surface of a nonporous support material wherein the palladium forms a thin, firm and adherent coating, thus obtaining maximum catalytic activity by means of a thin, peripheral distribution of palladium oxide in the support material. The resulting catalyst was taught as useful in removing traces of oxygen from hydrogen by converting the oxygen to water. U.S. Pat. No. 3,328,465 to Spiegler teaches the preparation of palladium metal deposited on nonporous carbon support admixed with a porous carbon. The resulting catalyst is taught as resulting in a rate of hydrogenation of nitro compounds to amines about twice that of a hydrogenation process using the same amount of palladium deposited on a nonporous carbon. Previously, carbon used for support of palladium had been mainly porous carbon of vegetable or animal origin. Due to the high porosity of the carbon, some of the palladium became trapped in the pores and did not contribute to the activity of the catalyst. Another disadvantage was that such porous catalysts became fouled with the products of hydrogenation.

Purification of phthalic acids by hydrogenation often has been over a catalyst prepared by the above methods of palladium or platinum metal upon a support which can be porous or nonporous. However, purification of terephthalic acid by hydrogenation using typical catalysts of palladium or platinum metal prepared in the usual methods can result in unacceptable levels of impurities in the purified acid.

The impurities in crude terephthalic acid prepared by oxidation of p-xylene are partially oxidized products such as 4-carboxybenzaldehyde and toluic acid. These compounds usually are present in significant amounts in the crude acid. 4-Carboxybenzaldehyde is a particularly undesirable impurity because it acts as a chainstopper during polyesterification of terephthalic acid. Although 4-carboxybenzaldehyde is difficult to remove by physical means, it can be hydrogenated to toluic acid and other derivatives. Toluic acid also acts as a chain stopper during polymerization of terephthalic acid. However, it can be efficiently readily removed by cooling and crystallizing terephthalic acid solutions containing it. The purification of terephthalic acid therefore often has been by hydrogenation using a Group VIII metal catalyst followed by a separation process to eliminate toluic acid. An accompanying problem accordingly has been to control the activity and selectivity of the Group VIII metal catalyst to obtain lower levels of toluic acid. Accordingly, a catalyst for a process is highly desirable whereby impurities such as 4-carboxybenzaldehyde are readily and selectively substantially removed from crude terephthalic acid without increasing the level of toluic acid.

A number of techniques and processes have been developed to purify terephthalic acid by hydrogenation using palladium or platinum catalysts conventionally prepared as described above.

U.S. Pat. No. 3,522,298 to Bryant, et al., teaches a process wherein crude terephthalic acid is admixed with an inert gaseous carrier such as steam. The vapor mixture is contacted at a temperature of from 600° to 1000° F. with hydrogen in the presence of a catalyst such as a Group VIII metal upon a carbonaceous support, i.e., palladium upon powdered carbon. Vaporized terephthalic acid is separated by condensation from other constituents in the vapor, e.g., steam, other impurities, U.S. Pat. No. 3,542,863 to Zimmerschied teaches that hot formic acid treatment of a palladium metal on charcoal catalyst controls the activity and/or reactivity in processes where oxygenated hydrocarbons such as aromatic acids are treated under reducing conditions and initial activity of a fresh catalyst is excessive, causing over-hydrogenation of aromatic rings or carboxylic acid groups. U.S. Pat. No. 3,584,039 to Meyer teaches purification of terephthalic acid by hydrogenation in aqueous liquid phase upon a Group VIII metal on carbon in the presence of hydrogen followed by crystallization from the mother liquor. U.S. Pat. No. 3,591,629 to Stancell, et al., teaches that a phenylbenzene treated catalyst of a Group VIII metal on activated carbon particles minimizes the conversion of terephthalic acid in the presence of hydrogen while effecting high conversions of 4-carboxybenzaldehyde contaminating the crude acid to compounds readily separable from the terephthalic acid. U.S. Pat. No. 3,607,921 to Stancell teaches that contact of crude terephthalic acid with palladium on carbon support in the presence of carbon monoxide, and, alternatively, hydrogen, effects a high percentage conversion of 4-carboxybenzaldehyde contaminating the acid into substances readily separable. Surface area of the metal upon the carbon support is taught as being extremely high, to 120 square meters per gram. U.S. Pat. No. 3,726,915 to Pohlmann teaches that copper based on palladium/carbon catalysts increases the effectiveness of palladium on carbon catalysts in hydrogenation of crude terephthalic acid in selective reduction of 4-carboxybenzaldehyde. U.S. Pat. No. 3,799,976 to Nienburg, et al., teaches purification of terephthalic acid containing 4-carboxybenzaldehyde by heating an aqueous mixture of the crude acid with formic acid in contact with a Group VIII metal on carbon as catalyst. U.S. Pat. No. 4,260,817 to Thompson, et al., teaches a method for purifying crude terephthalic acid by hydrogenating the crude acid in aqueous solution to make toluic acid from 4-carboxybenzaldehyde and p-xylene from terephthalyl dialdehyde wherein the reduction takes place in two stages, the aldehyde radical forming an alcohol radical and in turn forming a methyl radical. The catalyst comprises two Group VIII metals on carbon particles.

Accordingly, it is well-known that crude terephthalic acid containing high levels of 4-carboxybenzaldehyde and other impurities can be purified by hydrogenation of 4-CBA to toluic acid over a Group VIII metal or metals on carbon catalysts. However, toluic acid levels are usually increased. Therefore, hydrogenation catalysts of improved selectivity are highly desirable. In severe evaluation tests of the invented catalysts, 4-carboxybenzaldehyde content of terephthalic acid can be reduced to less than 70 ppm and p-toluic acid content remains at a level of less than 2000 ppm.

SUMMARY

A process for producing a purified terephthalic acid which comprises reacting in a liquid phase a mixture of hydrogen and crude terephthalic acid in the presence of a catalyst compound comprising a palladium/rhodium metal catalyst at a temperature of from about 100° to about 300° C. and a pressure from about 200 to about 1500 psi, wherein the catalyst compound is prepared by adsorbing palladium on a porous carbonaceous support from a solution of a comlex palladium salt formed in the presence of an amine and acetic acid, followed by deposition of rhodium from a solution of sodium hexanitritorhodate.

DETAILED DESCRIPTION OF THE INVENTION

The process of the instant invention relates to purification of terephthalic acid in the presence of a palladium/rhodium catalyst. In a severe evaluation test, crude terephthalic acid containing up to 10,000 ppm of 4-carboxybenzaldehyde is hydrogenated, 4-carboxybenzaldehyde (4-CBA) content is decreased to less than 100 ppm and increase in toluic acid content is minimized. The general method requires use of a palladium/rhodium catalyst prepared by deposition of a complex palladium salt upon a porous carbonaceous substrate having a surface area of at least 600 m$^2$/g, followed by deposition of a rhodium salt. The complex salt is prepared by dissolving palladium chloride or another palladium salt in water in the presence of an amine, followed by addition of an organic carboxylic acid. The rhodium salt is deposited from an aqueous solution prepared from a rhodium salt such as rhodium chloride and sodium nitrate.

It has been found that catalysts prepared by the above method are effective in purifying crude terephthalic acid. In a severe evaluation test, a catalyst of palladium/rhodium on a porous carbonaceous substrate, prepared by the above method, is selective in the presence of hydrogen in reducing 4-carboxybenzaldehyde content to levels of less than 100 parts per million (ppm) and maintaining p-toluic acid content at less than 2000 ppm.

Palladium and rhodium are the preferred metals for the catalyst of this invention, but other metals of Group VIII of the Periodic Table of Elements and possessing activity for hydrogenation are suitable in general, such as ruthenium, osmium, iridium and platinum. The pertinent Periodic Table of Elements can be found on the inside of the back cover of HANDBOOK OF CHEMISTRY AND PHYSICS, 46th edition, Robert C. Weast, Editor, Chemical Rubber Company, Cleveland, Ohio (1965).

Ammonia and organic amines can be used to make a water soluble complex salt of palladium suitable for preparation of catalysts of the instant invention. The organic amines can be aliphatic, aromatic, or heterocyclic. Preferred organic amines are pyridine, picolines, lutidines, etc. Use of these amines causes palladium to be adsorbed quickly and almost quantitatively on coconut charcoal, in contrast to use of ammonium complexes of palladium salts, or ethylene diamine complexes of palladium salts, wherein adsorption of palladium on coconut charcoal under similar conditions is only in the 37 to 68% range. However, catalysts so prepared are still active catalysts in the hydrogenation of 4-carboxybenzaldehyde.

As indicated, the novel process of the present invention is carried out using an organic carboxylic acid, either monocarboxylic or polycarboxylic. This includes both lower aliphatic saturated fatty acids which are liquids at room temperature (about 25° C.) and, particularly, saturated fatty monocarboxylic acids having from 2 to 5 carbon atoms, inclusive, such as acetic acid, proprionic acid, butyric acid, isobutyric acid, n-valeric acid and the like, and higher aliphatic saturated fatty acids which, although solids at room temperature, can be dissolved in the presence of amines, such as lauric acid, myristic acid, palmitic acid, stearic acid, malonic acid, glutaric acid, pimelic acid, azelaic acid and the like. Unsaturated acids and inorganic acids may also be useful for this purpose.

The porous carbonaceous support or substrate is any suitable granular carbon having a surface area of at least 600 m$^2$/g. Activated carbon granules of high surface area prepared from plant, animal or mineral sources can be used. While carbon granules are preferred, the method of this invention would also extend to carbon used in the form of pellets and other particulate forms. Preferably, the substrate is activated carbon of plant or animal origin, most preferably of coconut charcoal.

For reasons unknown, a more selective catalyst is obtained by the addition of an organic carboxylic acid such as acetic acid to an aqueous solution of an amine complex of a palladium salt during catalyst preparation.

Preferably, the palladium component of the catalyst of this invention is prepared from aqueous solutions of amine complexes of a palladium salt in the presence of acetic acid wherein the acetic acid and amines are present in substantially equimolar quantities. The palladium is adsorbed upon the surface of activated carbon granules over a period of from 1 to 24 hours. The resulting composition comprising the palladium on activated carbon is washed, filtered and dried. A water slurry of the palladium/carbon composition is thereupon prepared to which a soluble complex rhodium salt made from a simple rhodium salt and sodium nitrite is added. The rhodium is adsorbed upon the surface of the palladium/carbon composition over a period of 1 to 24 hours under slow agitation. The resulting composition comprising palladium/rhodium crystallites on activated carbon is washed, filtered and dried. Before evaluation, the catalyst is subjected to a hydrogen treatment. A water slurry of the freshly prepared catalyst is heated with hydrogen, for a period of about 1¾ to 2 hours at a temperature of 270° C. After the composition is cooled, the catalyst particles are filtered and dried under vacuum at approximately 80° C.

For reasons which are not understood, it has been found that hydrogenation of crude terephthalic acid with a catalyst comprising palladium/rhodium metal crystallites upon activated carbon preferably prepared from an aqueous solution of a palladium chloride salt, pyridine and acetic acid, followed by treatment with an aqueous solution of a complex salt of a rhodium chloride with a stoichiometric amount of sodium nitrite purifies crude terephthalic acid by decreasing the content of 4-carboxybenzaldehyde (4-CBA) to less than 100 parts per million and p-toluic acid is less than 2,000 parts per million in a severe test evaluation wherein crude terephthalic acid contains about 8000 ppm 4-CBA and about 1500 ppm p-toluic acid.

The catalysts of the instant invention are preferably prepared in two sequential steps: first, the palladium is introduced on the surface of the active carbon, followed by introduction of the rhodium. The two metals can be introduced, less preferably, in one step. The two step sequential preparation as described above results in a more selective catalyst. Evidence indicates the presence of palladium crystallites upon the surface of the active carbon influences the penetration of rhodium metal crystallite particles into the carbon. Electron microprobe analyses indicate that rhodium metal or particles penetrate 200 to 300 micrometers into the surface of microporous coconut charcoal containing no palladium. Penetration of rhodium metal particles from the same precursor solution is within the range of from 70 to 150 micrometers of the surface of the microporous support when microporous coconut charcoal has palladium metal particles on the surface of the microporous coconut charcoal. Depth of penetration of palladium and rhodium metal crystallite particles is of approximately the same depth. Accordingly, it is an object of this invention to regulate the penetration of a Group VIII metal, such as rhodium, into a microporous coconut charcoal in the presence of a second Group VIII metal, such as palladium. It accordingly is a further object of this invention to regulate penetration of two or more Group VIII metals into microporous coconut charcoal to obtain a hydrogenation catalyst of improved selectivity in hydrogenating 4-carboxybenzaldehyde.

The palladium salt utilized in the present invention is typically a palladium halide such as palladium chloride, palladium bromide, and palladium iodide, or palladium acetate. The palladium salt is dissolved in an aqueous solution containing an amine compound. Concentration of the amine compound is at a level sufficient to solubilize the palladium salt. An organic carboxylic acid, preferably an aliphatic saturated fatty acid, more preferably acetic acid, is then added to the solution. Mole ratio of the acid to the amine is at least 0.75. The resulting solution is thereupon added to an activated carbon-water mixture with stirring. The resulting palladium/carbon particles are then filtered and dried. For introduction of the rhodium component, the palladium/carbon particles are slurried in water and a previously-prepared aqueous solution of rhodium halide in water containing an alkali metal nitrite is added with slow agitation. Concentration of the alkali metal nitrite is sufficient to solubilize the rhodium halide. The resulting palladium/rhodium/carbon particles are filtered, washed and dried. Rhodium halides such as rhodium chloride, rhodium bromide and rhodium iodide can be used. Alkali metal nitrite salts such as sodium nitrite and potassium nitrite can be used.

It has been found that use of an amine and an organic carboxylic acid, such as acetic acid, in approximately equimolar quantities in preparation of the instant catalyst results in a hydrogenation catalyst which in a standard laboratory test reduces 4-CBA content of up to 10,000 ppm in crude terephthalic acid to a level below 100 ppm and p-toluic acid content is not substantially increased.

It has been found that not to use an organic carboxylic acid, such as acetic acid, in the preparation of the palladium/carbon component results in considerably higher levels of 4-carboxybenzaldehyde in the purified terephthalic acid in the standard test procedure. It has been found that to use a palladium catalyst prepared in the above manner but without the presence of rhodium results in acceptable levels of 4-carboxybenzaldehyde but that levels of p-toluic acid cannot be controlled to minimal levels.

The support upon which the palladium salt is deposited is preferably a coconut charcoal in the form of granules of surface area of at least 600 m$^2$/g (N$_2$, BET method) although other porous carbonaceous materials can be used such as activated carbon of plant origin, animal origin or mineral origin.

Palladium and rhodium content of the carbon granules using the method of preparing the instant catalyst is usually less than 1.0 (wt) percent of total catalyst weight, preferably less than 0.60 (wt) percent of total catalyst weight. Higher concentrations of metals can be deposited but apparently are of little avail because in the process of reducing 4-CBA content of crude terephthalic acid, the lower concentrations of palladium/rhodium metals provide an efficient catalyst.

In summary, the instant invention comprises a method of preparing a catalyst composition, the catalyst composition prepared thereby, and a catalytic hydrogenation process for hydrogenating crude terephthalic acid containing up to 10,000 ppm of 4-carboxybenzaldehyde in the presence of the catalyst composition, water and hydrogen at a temperature of from about 100° C. to 300° C. and a pressure of from about 200 to 1500 psi, and recovering purified terephthalic acid from the mixture. The catalyst is prepared by contacting porous carbonaceous support granules with an aqueous solution of an amine and a palladium salt in the presence of an organic carboxylic acid, preferably an aliphatic saturated fatty acid, and an aqueous solution of a rhodium compound and an alkali metal nitrite. Concentration of said amine is sufficient to solubilize the palladium salt. Mole ratio of the acid to amine is at least 0.75, preferably approximately 1.0. Concentration of the alkali metal nitrite is sufficient to solubilize the rhodium salt. Preferably the porous carbonaceous support is activated carbon of plant or animal origin having a surface area of at least 600 m$^2$/g. Most preferably, the activated carbon is a coconut charcoal.

The invention will be further illustrated by reference to the following specific examples.

EXAMPLE 1

A number of catalysts were prepared to illustrate the present invention. In all cases approximately 4 to 8 mesh granular carbons of coconut shell origin were washed with distilled water to remove fines and then drained. The carbons were contacted with the solutions as indicated below, washed, drained and dried at a temperature of approximately 80° C.

Catalyst A. Granular coconut charcoal (12 g) was washed with distilled water to remove the carbon fines. The water was decanted and the moist charcoal was transferred into a 3-necked 300 ml flask. Distilled water (40 ml) was placed over it. A glass stirrer was installed which had a small paddle immersed into the water layer above the carbon. The stirrer was turned on. Palladium chloride (0.202 g) was dissolved in a mixture of distilled water (22.0 ml) and conc. ammonium hydroxide solution (3.0 ml with 28–30 (wt) % NH$_3$). This solution was added dropwise from a dropping funnel to the stirred charcoal-water mixture. The stirring was continued for 2¾ hours. Then the catalyst was filtered, washed with water and dried in vacuum at 80° C.

Catalyst B. Granular coconut charcoal (18.0 g) was washed with distilled water to remove the carbon fines. The water was decanted and the moist charcoal was transferred into a 3-necked 300 ml flask. Distilled water (60.0 ml) and acetic acid (0.05 ml) were placed over it and stirred with a paddle located in the water layer above the carbon. From a dropping funnel, a solution of PdCl$_2$ (0.153 g) in water (40.0 ml) containing a mixture of pyridine (0.5 ml) and acetic acid (0.20 ml) was introduced dropwise and stirred for 1¾ hours. Then the resulting catalyst was filtered, washed with distilled water and dried in vacuum at 80° C. Acetic acid/pyridine mole ratio was 0.66.

Catalyst C. In the method of Catalyst A, Catalyst C was prepared from $PdCl_2$, ammonia and acetic acid as follows: $PdCl_2$ (0.202 g), water (60 ml), ammonia (3.0 ml with 28-30 (wt) % $NH_3$), acetic acid (3.6 ml). Acetic acid/ammonia mole ratio was 1:1.13.

Catalyst D. In the method of Catalyst B, Catalyst D was prepared from $PdCl_2$, pyridine, acetic acid as follows: $PdCl_2$ (0.153 g), water (100 ml), pyridine (0.75 ml), acetic acid (0.55 ml). Acetic acid/pyridine mole ratio was 1:1.

Catalyst E. In the method of Catalyst D, Catalyst E was prepared from $PdCl_2$ and pyridine as follows: $PdCl_2$ (0.153 g), water (100 ml), pyridine (0.75 ml).

Catalyst F. Granular coconut charcoal (b 12.0 g) was washed with distilled water to remove the carbon fines. The water was decanted and the moist charcoal was transferred into a 3-necked 300 ml flask. Distilled water (40.0 ml) was placed over it. A glass stirrer was installed as in the procedure for Catalyst A and turned on. Rhodium chloride dissolved in water (60.0 ml) with sodium nitrite (0.074 g $RhCl_3$, 0.148 g $NaNO_2$, molar ratio 1:4) was added to the flask. The stirring was continued for 2 hours. Then the catalyst was filtered, washed with water and dried in vacuum at 80° C.

Catalyst G. Catalyst G was prepared in two stages. In the first stage palladium was deposited on the charcoal by the method of Catalyst E from $PdCl_2$ and pyridine. In the second stage rhodium was deposited from an aqueous solution of $RhCl_3$ made with the aid of $NaNO_2$.

Distilled water (100 ml) was poured over 18.0 g granular (4×8 mesh) coconut charcoal and the mixture was swirled. After the effervescence ceased, the mixture was filtered through a coarse stainless steel wire gauze filter and the carbon was washed with distilled water. This operation removed some carbon fines. The wet carbon was then transferred into a 3-necked 300 ml flask and 60 ml distilled water was placed over it. The aqueous layer above the carbon was agitated with a stirrer which also caused some movement of the carbon granules in the lower layers.

Palladium chloride ($PdCl_2$, 92 mg) was dissolved in a mixture of water (5 ml) and pyridine (0.95 ml). This solution was diluted with water to 35.0 ml volume. It was then added to the carbon-water mixture and stirred for 2 hours. Then the resulting Pd/C composition was filtered, was washed with water and was dried in vacuo at 80° C.

For the introduction of the rhodium component, the Pd/C composition was placed into a 3-necked flask, 60 ml of distilled water was added and the upper water layer was agitated. Then a solution of $RhCl_3$ (74 mg) plus $NaNO_2$ (150 mg) in 35 ml distilled water was introduced dropwise. After 3 hours stirring, the resulting Pd-Rh/C catalyst was filtered, washed with distilled water and dried in vacuo at 80° C. (17.5 g). This catalyst had ≦0.3 (wt) % Pd content and ≦0.2 (wt) % Rh content (based on analyses of the filtrates).

Catalyst H. Catalyst H was prepared in two stages as was Catalyst G. Details were as follows:

Distilled water (100 ml) was poured over 18.0 g granular (4×8 mesh) coconut charcoal and the mixture was swirled. After the effervescence ceased, the mixture was filtered through a coarse stainless steel wire gauze filter and the carbon was washed with distilled water. This operation removed some carbon fines. The wet carbon was then transferred into a 3-necked 300 ml flask and 60 ml distilled water was placed over it. The aqueous layer above the carbon was agitated with a stirrer which also caused some movement of the carbon granules in the lower layers.

Palladium chloride ($PdCl_2$, 92 mg) was dissolved in a mixture of distilled water (5 ml) and pyridine (0.5 ml). Then 0.35 ml glacial acetic acid was added and the volume of the solution was diluted to 35 ml with distilled water. This solution was added dropwise to the stirred carbon-water mixture and stirred for 2 hours. Then the resulting Pd/C composition was filtered, was washed with water and was dried in vacuo at 80° C.

For the introduction of the rhodium component, the Pd/C composition was placed into a 3-necked flask, 60 ml of distilled water was added and the upper water layer was agitated. Then a solution of $RhCl_3$ (74 mg) plus $NaNO_2$ (150 mg) in 35 ml distilled water was introduced dropwise. After 3 hours stirring, the resulting Pd-Rh/C catalyst was filtered, washed with distilled water and dried in vacuo at 80° C. (17.5 g). This catalyst had ≦0.3 (wt) % Pd content and ≦0.2 (wt) % Rh content based on analyses of the filtrates).

To standardize the laboratory evaluation of the catalysts, to give "simulated aging," the above catalysts were hydrogenated in the following procedure:

Distilled water (150 ml), the catalyst (6.0 g) and hydrogen gas at 200 psig were charged into a 300 ml rocking autoclave, heated to 270° C. and held at that temperature for 1¾ hours. After cooling, the catalyst was recovered and dried in a vacuum oven at 80° C.

In a simulation of a plant hydrogenation process, the above catalysts were evaluated for terephthalic acid (TA) purification in a standard laboratory test. Catalyst and crude terephthalic acid were charged into a 300 ml rocking autoclave as follows: 12.9 g of crude TA, containing 7900 ppm 4-carboxybenzaldehyde (4-CBA) and 1460 ppm of p-toluic acid; 150 ml distilled water; 0.17 g of catalyst under evaluation and 200 psig hydrogen gas. The reactor was heated to 250° C. and held at that temperature for 3½ hours. After cooling, the TA crystals were filtered, washed with 100 ml distilled water and dried in vacuo at 105° C. The purified TA was analyzed by liquid chromatography and by polargraphy. Results are in Table I. A commercially available palladium/carbon catalyst was used as a comparative example.

TABLE I

| Catalyst and Run No. | Precursors to Catalyst | 4-CBA (ppm) | Acetic Acid/ Amine Molar Ratio | (wt) % Pd or Rh | p-Toluic Acid |
|---|---|---|---|---|---|
| Commercial | Pd/Carbon | 153 | — | 0.50a | — |
| A-5054-180-1 | $PdCl_2/NH_3$ | 423 | 0 | 0.25a | 1390 |
| B-5293-5-1 | $PdCl_2$/Pyridine/Acetic Acid (Trace) | 394 | 0.66 | 0.50a,c | 5227 |
| C-5054-183-1 | $PdCl_2/NH_3$/Acetic Acid | 91 | 1.13 | 0.36a | 2411 |
| D-5054-125-1-5293-33-1 | $PdCl_2$/Pyridine/Acetic Acid | 47 34 | 1.00 | 0.50a | 9259 2607 |
| E-5054-186-1 | $PdCl_2$/Pyridine | 245 | 0 | 0.53a | 4407 |
| F-5054-78-2 | $RhCl_3/NaNO_2$ | 466 | — | 0.23b | — |
| G-5293-50 | $PdCl_2$/Pyridine/$RhCl_3$/$NaNO_2$ | 447 | 0 | 0.3a,c 0.2b,c | 1847 |
| H-5293-51 | $PdCl_2$/Pyridine/Acetic Acid/$RhCl_3$/ | 40 | 1.07 | 0.3a,c 0.2b,c | 1342 |

TABLE I-continued

| Catalyst and Run No. | Precursors to Catalyst | 4-CBA (ppm) | Acetic Acid/ Amine Molar Ratio | (wt) % Pd or Rh | p-Toluic Acid |
|---|---|---|---|---|---|
| | NaNO$_2$ | | | | |

Note:
a is palladium
b is rhodium
c means estimated value

The crude terephthalic acid used in the catalyst evaluation runs had 7900 ppm 4-carboxybenzaldehyde and 1460 ppm p-toluic acid content.

What is claimed is:

1. A process for purifying crude terephthalic acid containing up to 10,000 ppm of 4-carboxybenzaldehyde wherein said 4-carboxybenzaldehyde content is decreased to less than 100 ppm and p-toluic acid content increase is minimized which comprises hydrogenating said crude acid at a temperature of from about 100° C. to about 300° C. and a pressure of from 200 to 1500 psi with hydrogen in the presence of a catalyst composition which comprises crystallites of palladium and rhodium adsorbed on a porous activated carbon support material, said support having a surface area of at least 600 m$^2$/g, wherein said catalyst composition is prepared by contacting said support with (a) an aqueous solution of an amine and a palladium salt in the presence of an organic carboxylic acid wherein concentration of said amine is sufficient to solubilize said palladium salt and mole ratio of said acid to said amine is at least 0.75 and with (b) an aqueous solution of a rhodium compound and an alkali metal nitrite wherein penetration of said palladium and rhodium crystallites into said porous support is within the range of from about 70 to 150 micrometers of the surface of said support.

2. The process of claim 1 wherein said amine is selected from the group consisting of ammonia, pyridine, the picolines, and the lutidines.

3. The process of claim 1 wherein said amine is pyridine.

4. The process of claim 1 wherein said acid has from 2 to 5 carbon atoms and is selected from the group consisting of acetic acid, propionic acid, butyric acid, isobutyric acid, n-valeric acid and mixtures thereof.

5. The process of claim 1 wherein said acid is acetic acid.

6. The process of claim 1 wherein said palladium and rhodium compounds are halides and are individually selected from the group consisting of chlorides, bromides and iodides.

7. The process of claim 6 wherein said palladium and rhodium halides are chlorides.

8. The process of claim 1 wherein said alkali metal nitrite is selected from the group consisting of sodium and potassium nitrite.

9. The process of claim 1 wherein said nitrite is sodium nitrite.

10. The process of claim 1 wherein said support is selected from the group consisting of plant origin carbon, animal origin carbon and mineral origin carbon.

11. The process of claim 1 wherein said support is coconut charcoal.

12. The process of claim 1 wherein said palladium salt is palladium chloride, said amine is pyridine, said acid is acetic acid, said rhodium salt is rhodium chloride, said alkali metal nitrite is sodium nitrite and said support is coconut charcoal.

* * * * *